United States Patent [19]
Fujimoto et al.

[11] Patent Number: 5,694,936
[45] Date of Patent: Dec. 9, 1997

[54] ULTRASONIC APPARATUS FOR THERMOTHERAPY WITH VARIABLE FREQUENCY FOR SUPPRESSING CAVITATION

[75] Inventors: Katsuhiko Fujimoto, Urawa; Yoshiharu Ishibashi, Tokyo; Mariko Shibata, Yokohama; Takuji Suzuki, Kawasaki, all of Japan; Satoshi Aida, Beaverton, Oreg.; Shiroh Saitoh, Kawasaki; Kazuya Okamoto, Yono, both of Japan

[73] Assignee: Kabushiki Kaisha Toshiba, Kawasaki, Japan

[21] Appl. No.: 528,263

[22] Filed: Sep. 14, 1995

[30] Foreign Application Priority Data

Sep. 17, 1994 [JP] Japan ................... 6-248480

[51] Int. Cl.$^6$ ................................................. A61N 7/00
[52] U.S. Cl. ...................... 128/660.03; 601/3; 607/97
[58] Field of Search .................. 128/660.03; 601/2–4; 607/97

[56] References Cited

U.S. PATENT DOCUMENTS

| | | |
|---|---|---|
| 4,689,986 | 9/1987 | Carson et al. ................ 73/19 |
| 5,150,711 | 9/1992 | Dory . |
| 5,247,935 | 9/1993 | Cline et al. . |
| 5,368,032 | 11/1994 | Cline et al. . |

OTHER PUBLICATIONS

G. Vallancien et al., Focal Extracorporeal Pyrotherapy Preliminary Experimental Results; Dec. 10, 1990; Progress in Urology (1991), 1, 84–88.

*Primary Examiner*—Marvin M. Lateef
*Assistant Examiner*—Eleni Mantis Mercader
*Attorney, Agent, or Firm*—Oblon, Spivak, McClelland, Maier & Neustadt, P.C.

[57] ABSTRACT

An ultrasonic diagnosis apparatus for raising tissue temperature for hypothermic treatments, including an ultrasonic source for generating an ultrasonic treatment wave and a driving means for driving the ultrasonic source such that a frequency of the ultrasonic treatment wave generated by the ultrasonic source changes with time. The frequency of the ultrasonic treatment wave is changed along the time axis. By this change in frequency, some bubbles formed by cavitation as a result of the ultrasonic treatment wave are divided, and some bubbles are collapsed and therefore eliminated. Side effect cavitation and spread of a thermal degeneration area is suppressed, and thermal degeneration can be accurately induced in a desired area, thereby realizing a reliable, safe ultrasonic thermotherapy. Since cavitation is positively suppressed, the total treatment period can be shortened because cavitation would otherwise interfere with and slow down the thermal degeneration process. Therefore, treatment throughput can be improved as compared with a case in which cavitation is left to naturally break and disappear.

22 Claims, 10 Drawing Sheets

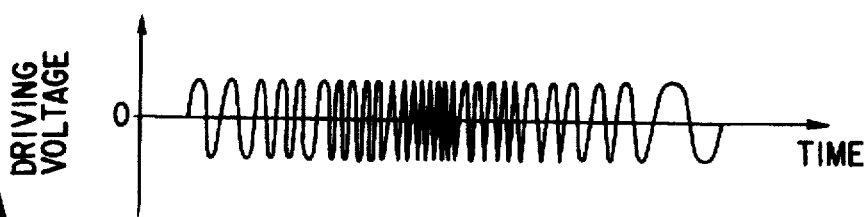
F I G. 3A
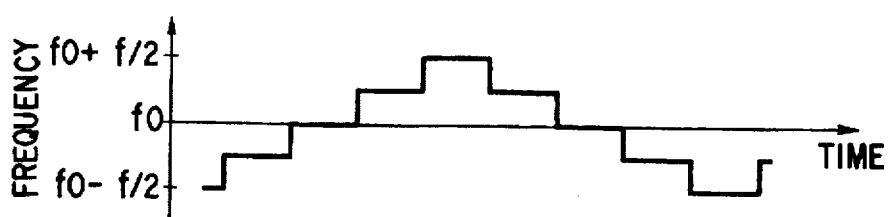
F I G. 3B
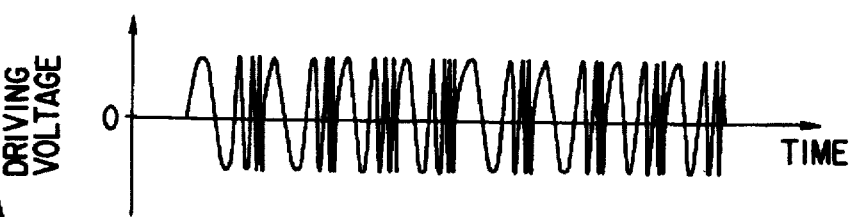
F I G. 4A
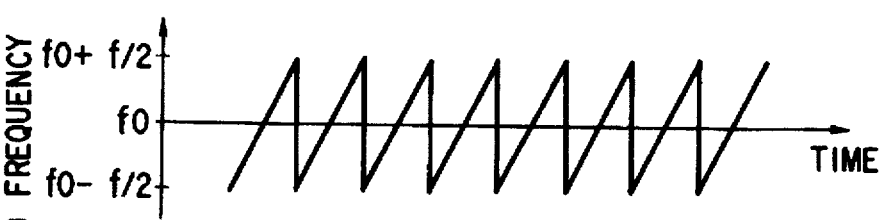
F I G. 4B
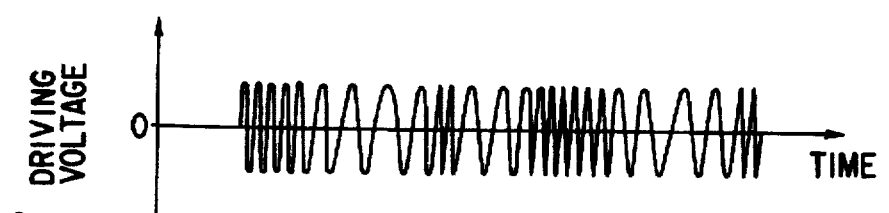
F I G. 5A
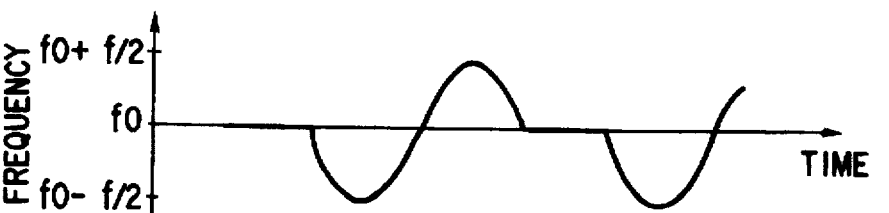
F I G. 5B

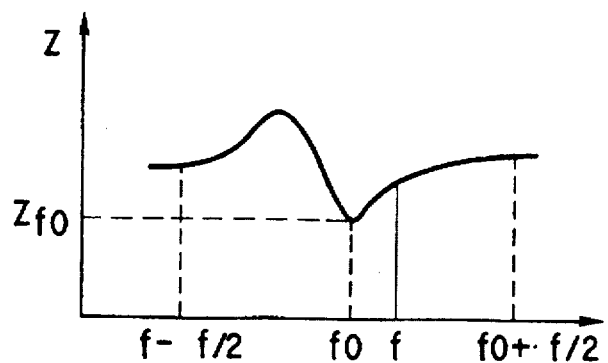
F I G. 6
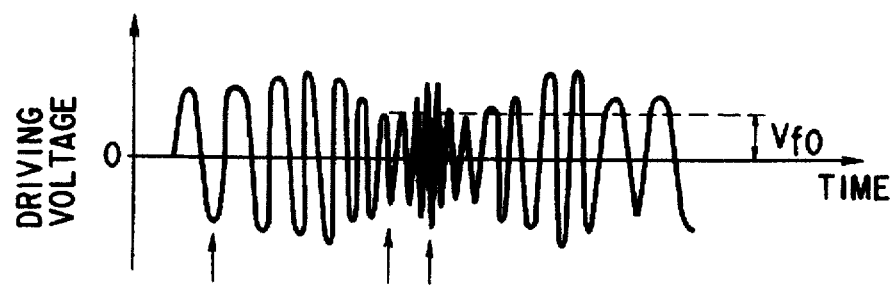
F I G. 7A
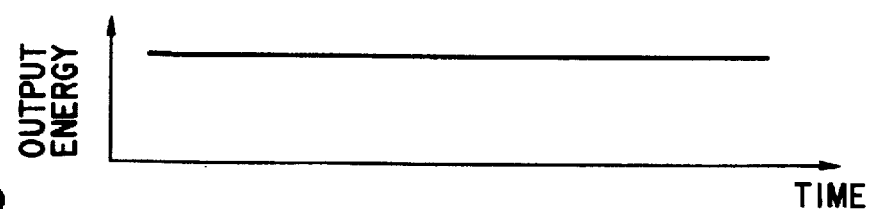
F I G. 7B
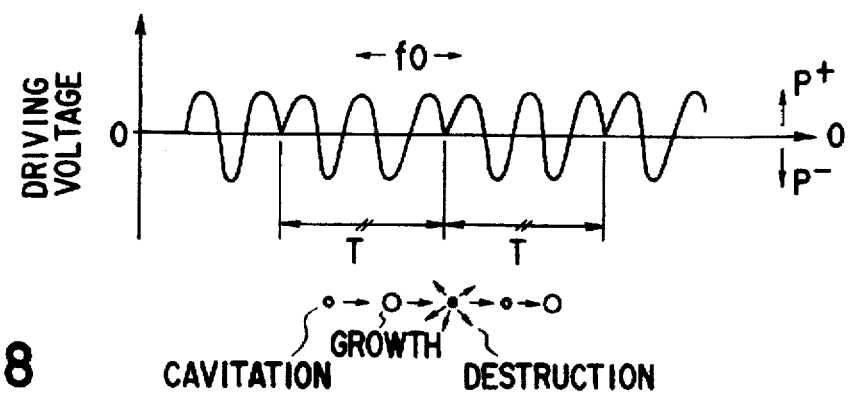
F I G. 8

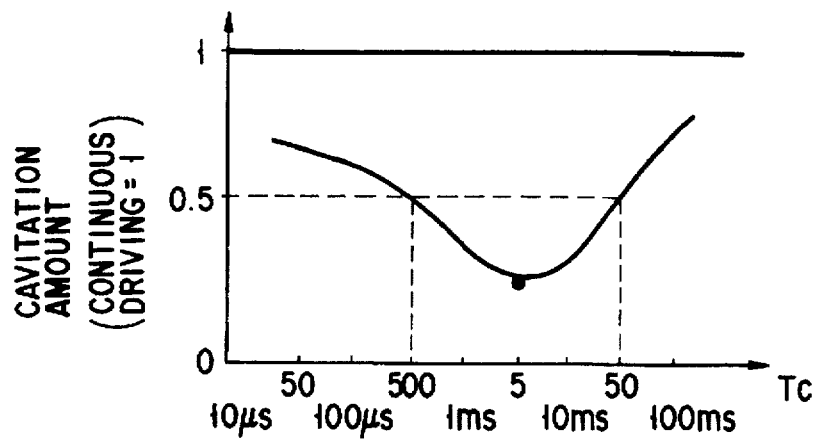
F I G. 12
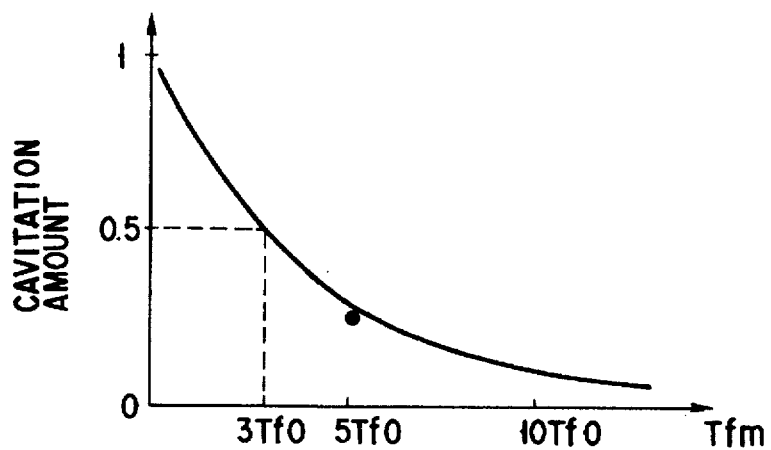
F I G. 13
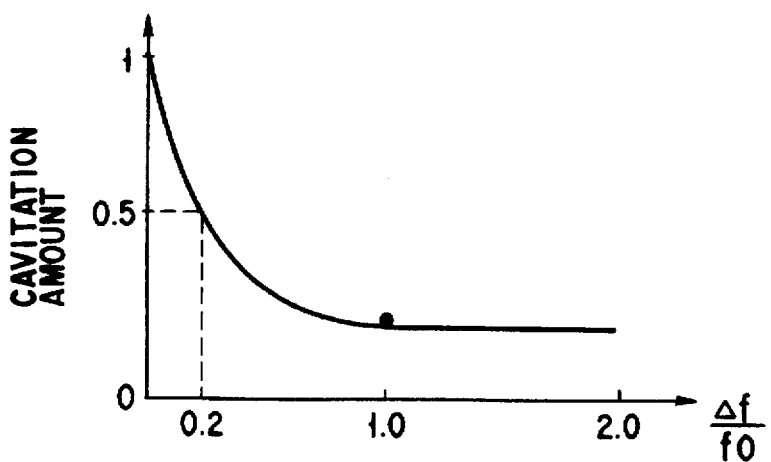
F I G. 14

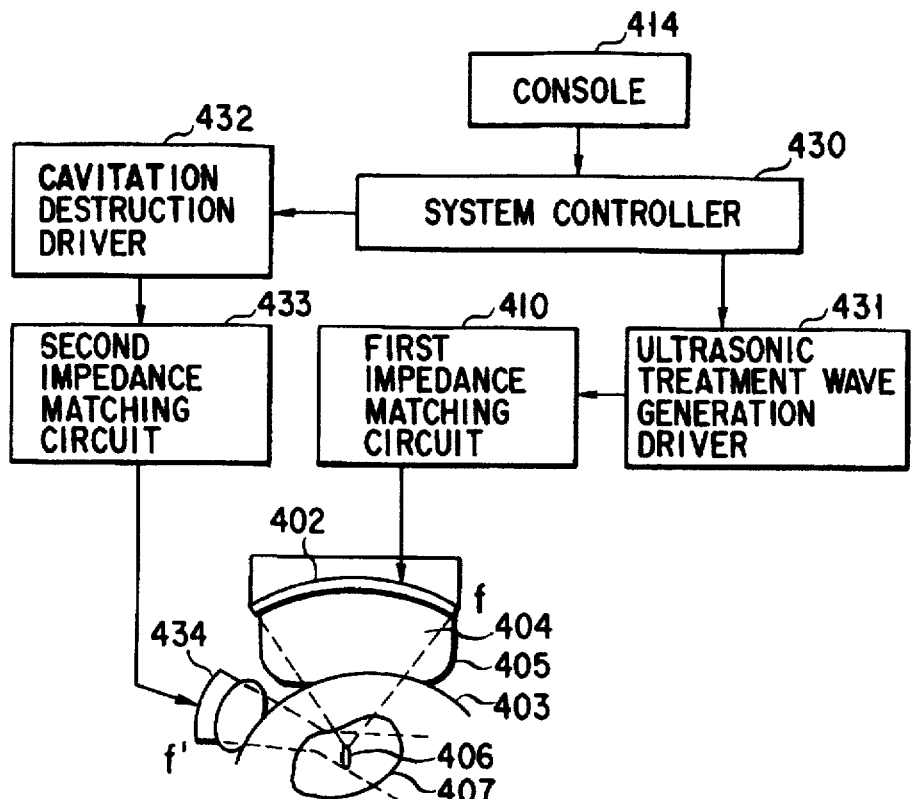
FIG. 15
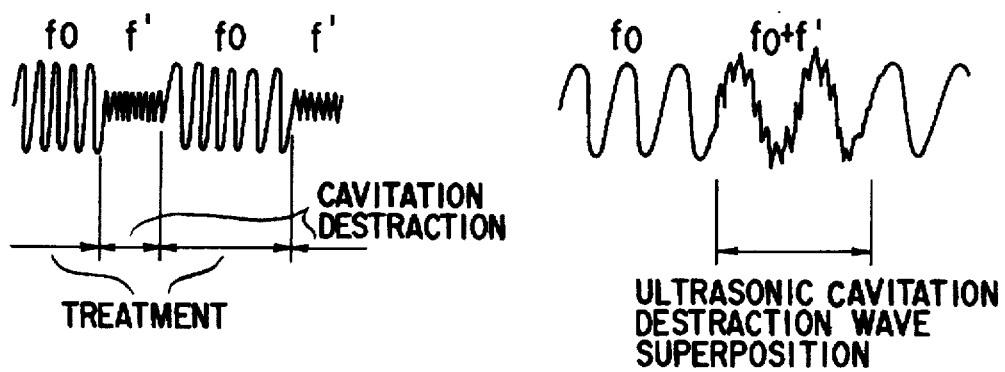
FIG. 16A
FIG. 16B
FIG. 16C

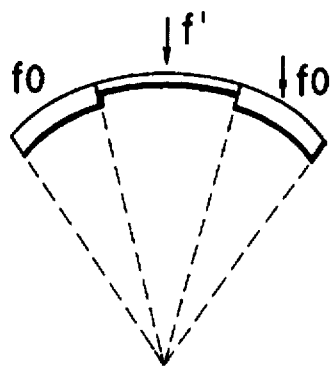
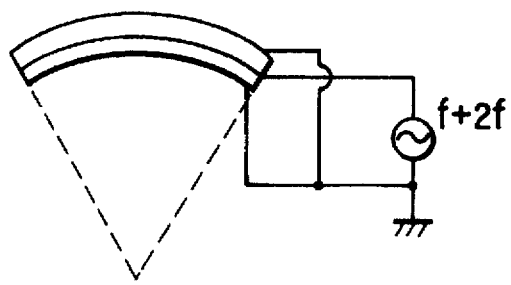
FIG. 17A     FIG. 17B
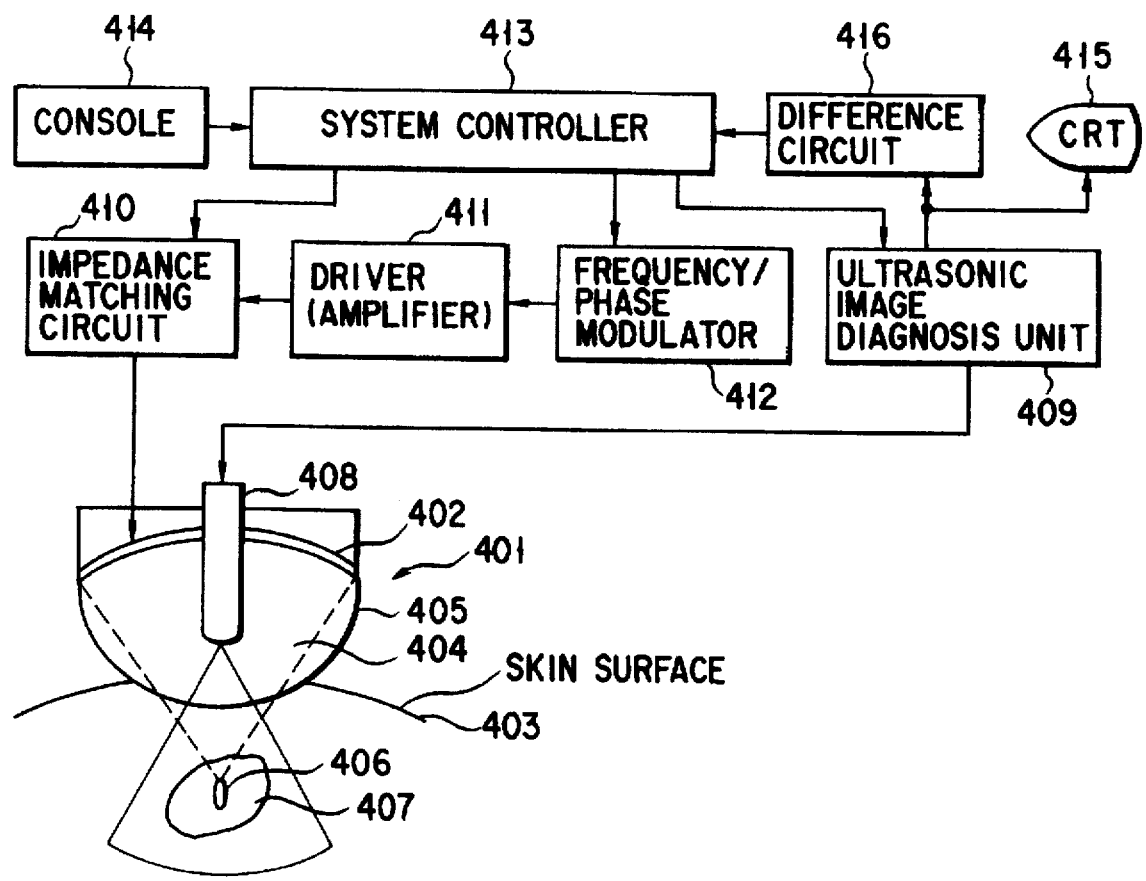
FIG. 18

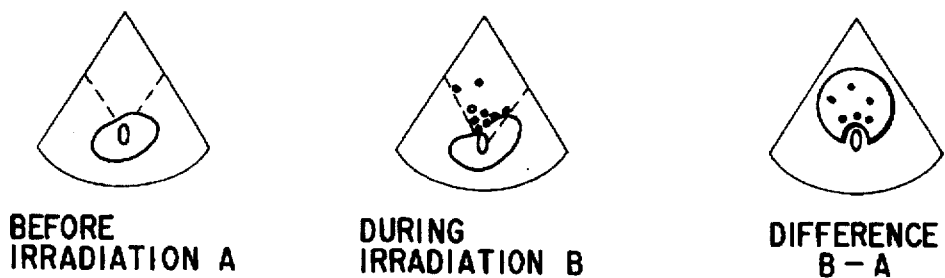
BEFORE IRRADIATION A
F I G. 19A
DURING IRRADIATION B
F I G. 19B
DIFFERENCE B − A
F I G. 19C
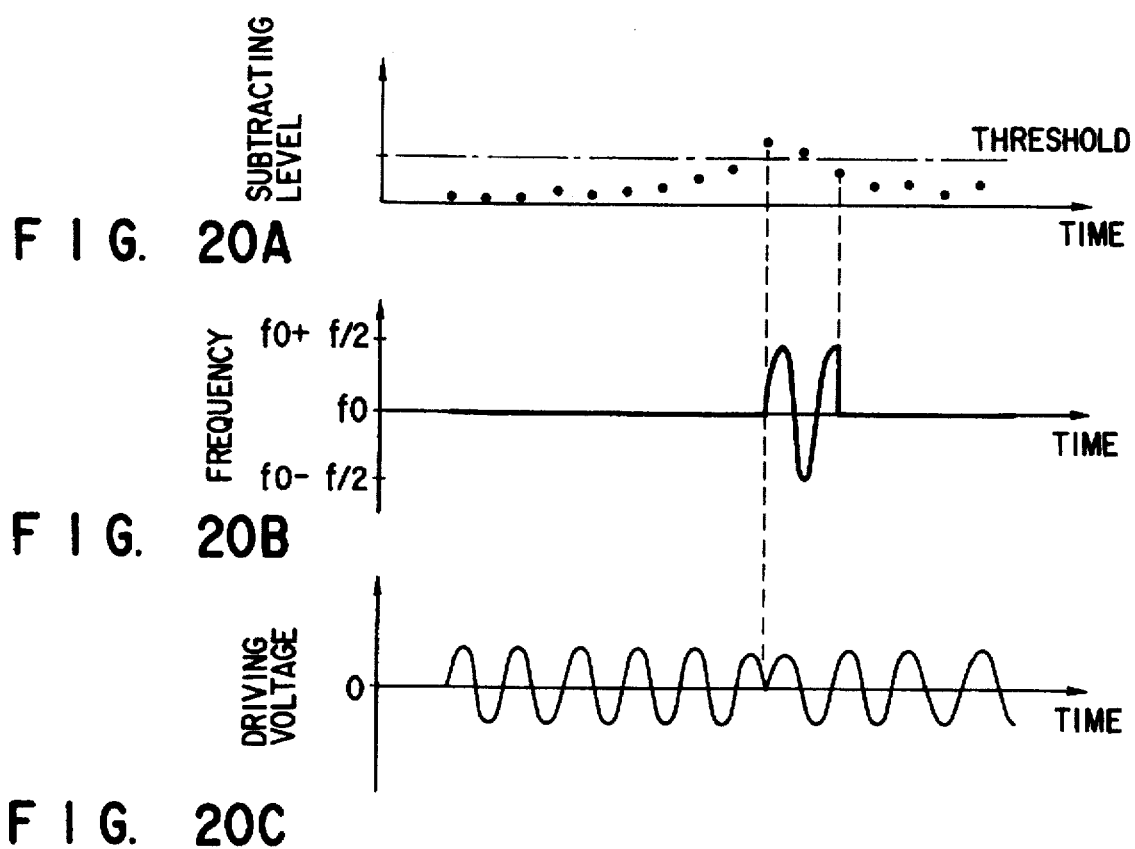
F I G. 20A
F I G. 20B
F I G. 20C

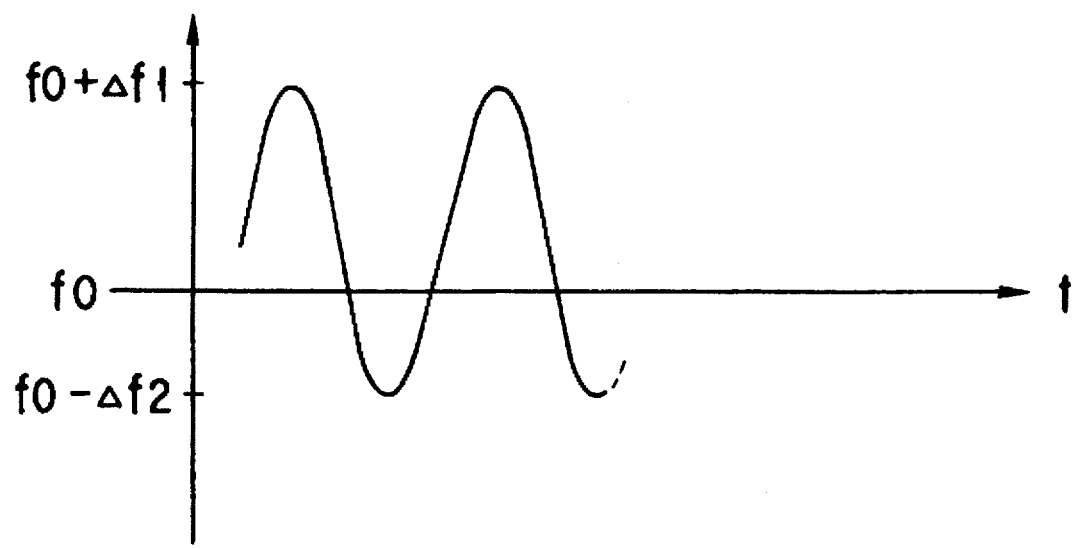
F I G. 21A
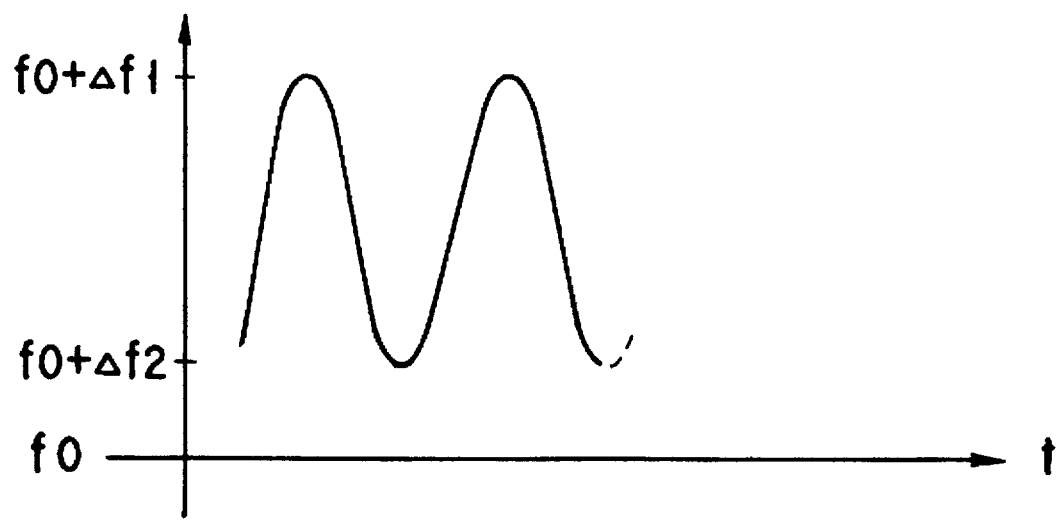
F I G. 21B

ULTRASONIC APPARATUS FOR THERMOTHERAPY WITH VARIABLE FREQUENCY FOR SUPPRESSING CAVITATION

BACKGROUND OF THE INVENTION

1. Field of the Invention

The present invention relates to an ultrasonic treatment apparatus for treating a tumor or the like in a living body using an ultrasonic wave.

2. Description of the Related Art

In recent years, an improvement of the quality of life (QOL) for patients after surgical operations has been demanded. With this trend, treatments categorized a minimally invasive treatment (MIT) has received a great deal of attention in the medical field.

An example of an MIT is a practical application of a lithotrite for irradiating a high-intensity extracorporeal ultrasonic wave on a stone to non-invasively break it, thereby greatly changing the therapy for urinary calculi. A high-intensity ultrasonic source used in such lithotrite is of a submerged discharge, electromagnetic induction, small-explosion, or piezoelectric type. In particular, although the piezoelectric ultrasonic source has a disadvantage in that the pressure of a high-intensity ultrasonic wave is low, it has the following advantages. The piezoelectric ultrasonic source can form a small focus spot, does not have any expendable components, can facilitate output control, can phase-control the driving voltages applied to a plurality of piezoelectric elements to arbitrarily control the focal position (Jpn. Pat. Appln. KOKAI Publication No. 60-145131 and U.S. Pat. No. 4,526,168).

In the therapeutic field of cancers, the MIT is one of the key words. Most cancer treatments currently depend on surgical operations. The functions and outer shapes of internal organs upon surgical operations often suffer greatly, which imposes great burdens on patients although they live on. Strong demand has therefore arisen for establishing an MIT and a treatment apparatus in consideration of the QOL.

Under these circumstances, a hyperthermia treatment has received an attention as one of malignant neoplasm, so-called cancer treatment techniques. According to this treatment method, utilizing a difference in caumesthesia between a tumor tissue and normal tissue, a morbid portion is heated to 42.5° C. or more and kept at this temperature to selectively kill only cancer cells. A method using an electromagnetic wave such as a microwave is popular as the heating method. However, this method is difficult to selectively heat a deep tumor due to the electrical characteristics of the living body. A good treatment effect cannot be expected for a tumor 5 cm or more deep from the skin surface. A method using ultrasonic energy which has excellent focusing characteristics and can reach a relatively deep portion is proposed as a method of treating a deep tumor (Jpn. Pat. Appln. KOKAI Publication No. 61-13955).

As an improvement of the above thermotherapy, there is also reported a treatment method of sharply focusing an ultrasonic wave generated by a piezoelectric element to heat a tumor portion to a temperature of 80° C. or more, thereby instantaneously thermally degenerating and necrotizing the tumor tissue (G. Vallancien et. al.: Progress in Uro. 1991, 1, 84–88 [EDAP papers], and U.S. Pat. No. 5,150,711).

According to this thermotherapy, unlike in the conventional hyperthermia, an ultrasonic wave having a very high intensity of, e.g., several hundred or thousand W/cm$^2$ is incident on a limited area near the focal point. For this reason, a specific phenomenon occurs in which cavitations (bubbles) are formed and the morbid portion qualitatively changes due to heat. By this specific phenomenon, the acoustic characteristics of the area change, the treatment effect may be decreased, and the treatment time may be prolonged.

Air is a highly reflective substance for an ultrasonic wave, and the ultrasonic wave cannot reach deeper than the area where bubbles are formed.

In the area where bubbles are formed, the ultrasonic wave is scattered and the apparent attenuation amount increases. For this reason, heat tends to be generated. When irradiation of a high-intensity ultrasonic wave is continued while cavitation are kept formed, an unwanted portion may be heated to cause a side effect.

As described in Jpn. Pat. Appln. KOKAI Publication No. 60-145131 and U.S. Pat. No. 4,658,828, high-intensity ultrasonic waves are intermittently irradiated at an interval corresponding to the time required for the cavitation to naturally break. This method, however, poses a problem of a long treatment time.

A morbid portion may be treated while the treatment progress and temperature are monitored by the MRI. However, the magnetic susceptibility of the portion under treatment changes in the presence of cavitation, and an error may occur.

SUMMARY OF THE INVENTION

It is an object of the present invention to provide an ultrasonic treatment apparatus capable of forcibly SUPPRESSING cavitation.

A related object of the present invention is to provide an ultrasonic treatment apparatus comprising: an ultrasonic source for generating an ultrasonic treatment wave; and driving means for driving the ultrasonic source such that a frequency of the ultrasonic treatment wave generated by the ultrasonic source changes along a time axis.

A further object of the present invention is to provide an apparatus according to claim 1, further comprising: means for scanning a slice of a target object with an ultrasonic beam to repeatedly generate ultrasonic images on the basis of resultant reception signals; difference means for obtaining a difference between two ultrasonic frame images generated at different times; and means for counting, on the basis of a difference result from the difference means, timings at which the frequency of the ultrasonic treatment wave is changed.

A still further object of the present invention is to provide an ultrasonic treatment apparatus comprising: an ultrasonic source for generating an ultrasonic treatment wave; and driving means for driving the ultrasonic source such that a phase of the ultrasonic treatment wave generated by the ultrasonic source is modulated.

Yet another object of the present invention is to provide an ultrasonic treatment apparatus comprising: a first ultrasonic source for generating an ultrasonic treatment wave; a second ultrasonic source for generating an ultrasonic cavitation destruction wave having a frequency higher than that of the ultrasonic treatment wave; and driving means for driving the first and second ultrasonic sources.

The frequency of the ultrasonic treatment wave is changed over time. By this change in frequency, some cavitation are divided, and some collapse to be destroyed. A side effect to an unwanted portion and a spread of the thermal degeneration area can be suppressed. At the same time, a desired portion can be accurately thermally degenerated, thereby realizing a reliable, safe ultrasonic thermotherapy. Since cavitation are positively destroyed, the total treatment time can be shorter than the time during which cavitation naturally break and disappear, thereby improving the throughput.

In addition, the phase of the ultrasonic treatment wave is changed. By this change in phase, growing cavitation collapses and is destroyed. A desired portion can be accurately thermally degenerated, thereby realizing a reliable, safe ultrasonic thermotherapy. Since cavitation are positively destroyed, the total treatment time can be shorter than the time during which cavitation naturally break and disappear, thereby improving the throughput.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 3A is a chart showing another waveform of the frequency-modulated driving signal along the time axis;

FIG. 3B is a chart showing a change in frequency of the driving signal in FIG. 3A along the time axis;

FIG. 4A is a chart showing still another waveform of the frequency-modulated driving signal along the time axis;

FIG. 4B is a chart showing a change in frequency of the driving signal in FIG. 4A along the time axis;

FIG. 5A is a chart showing still another waveform of the frequency-modulated driving signal along the time axis;

FIG. 5B is a chart showing a change in frequency of the driving signal in FIG. 5A along the time axis;

FIG. 6 is a graph showing the relationship between the frequency and the impedance;

FIG. 7A is a chart showing the waveform of an amplitude-modulated driving signal along the time axis;

FIG. 7B is a chart showing a change in output energy of an ultrasonic wave generated by the driving signal in FIG. 7A along the time axis;

FIG. 8 is a chart showing the waveform of a phase-modulated driving signal along the time axis;

FIG. 12 is a graph showing the relationship between the cycle time, Tc, and the residual cavitation amount;

FIG. 13 is a graph showing the relationship between the frequency modulation time, Tfm, and the residual cavitation amount;

FIG. 14 is a graph showing the relationship between the frequency modulation width and the residual cavitation amount;

FIG. 15 is a block diagram showing an arrangement according to the third embodiment of the present invention;

FIG. 16A is a chart showing the waveform of a driving signal as time-divisional treatment and cavitation destruction driving signals along the time axis;

FIG. 16B is a chart showing one waveform of a driving signal obtained by superposing the cavitation destruction driving signal and the treatment driving signal;

FIG. 16C is a chart showing another waveform of a driving signal obtained by superposing the cavitation destruction driving signal and the treatment driving signal;

FIG. 17A is a sectional view of an ultrasonic source showing an arranging relationship between two types of piezoelectric elements having different resonance frequencies;

FIG. 17B is a sectional view of an ultrasonic source showing another arranging relationship between two types of piezoelectric elements having different resonance frequencies;

FIG. 18 is a block diagram showing an arrangement according to the fourth embodiment of the present invention;

FIG. 19A is a view illustrating a mask image before ultrasonic irradiation;

FIG. 19B is a view illustrating a real-time image during ultrasonic irradiation;

FIG. 19C is a view illustrating a difference image between the mask image and the real-time image;

FIG. 20A is a chart showing a change in difference level along the time axis;

FIG. 20B is a chart showing a timing at which frequency modulation is started;

FIG. 20C is a chart showing a timing at which phase modulation is started; and

FIGS. 21A and 21B are charts showing a change in frequency of the driving signal.

DETAILED DESCRIPTION OF THE PREFERRED EMBODIMENTS

Preferred embodiments of the present invention will be described with reference to the accompanying drawings.

(First Embodiment)

Figure 1:
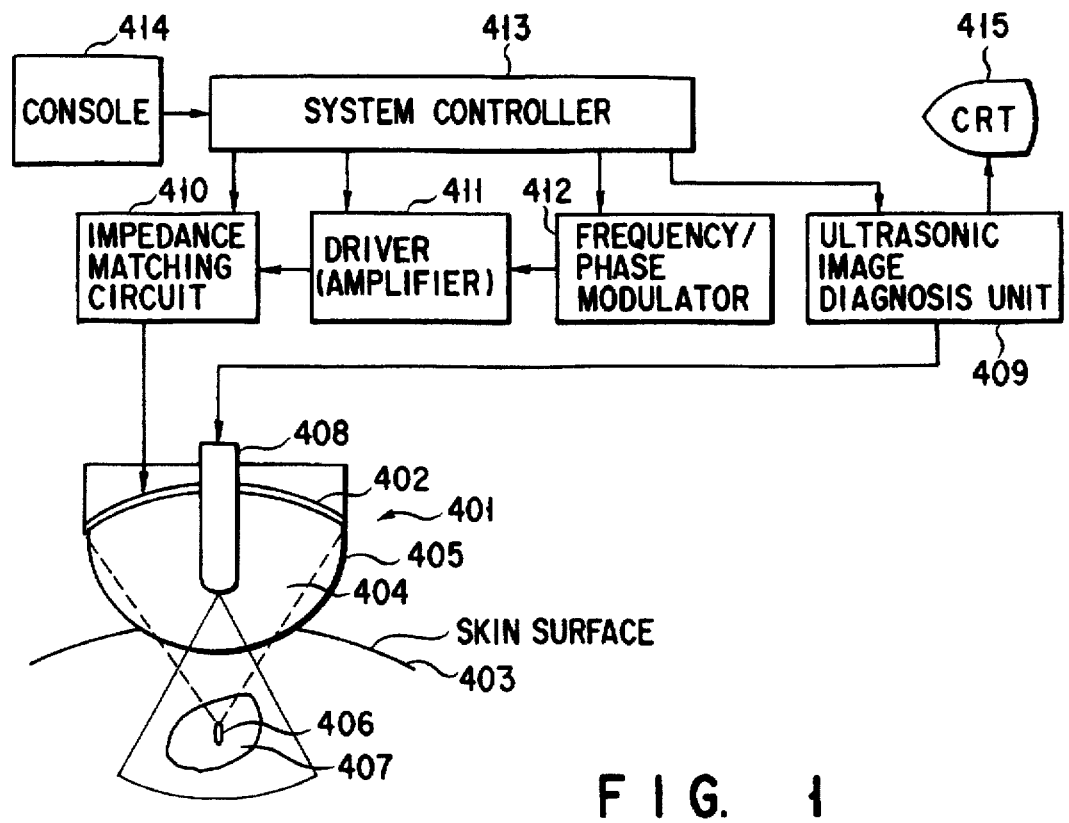
FIG. 1 is a block diagram showing an arrangement according to the first embodiment of the present invention.

FIG. 1 is a view showing the arrangement of an ultrasonic treatment apparatus according to the first embodiment of the present invention. The ultrasonic treatment apparatus is a thermotherapy apparatus for continuously irradiating an ultrasonic treatment wave on a morbid portion for a relatively long period of time to heat the morbid portion, thereby treating the morbid portion.

An applicator 401 has an ultrasonic source 402 for generating an ultrasonic treatment wave having a relatively high output level. The ultrasonic source 402 has a plurality of piezoelectric elements. The plurality of piezoelectric elements are arranged in a spherical pattern so as to focus ultrasonic treatment waves from the respective elements at a focal point 406.

A water bag 405 is mounted on the focal point side of the ultrasonic source 402. A coupling solution 404 is sealed in the bag 405 so that an ultrasonic treatment wave generated by the ultrasonic source 402 is guided onto a target object 403 with little loss. The central portion of the ultrasonic source 402 is notched, and an ultrasonic imaging probe 408 for confirming the position of a morbid portion 407 is inserted in the central notch of the ultrasonic source 402. An ultrasonic tomograph 409 scans the interior of the target object 403 with an ultrasonic beam through the ultrasonic imaging probe 408 to obtain an ultrasonic tomogram (B-mode image) near the focal point. The ultrasonic tomogram is visually displayed as a halftone image on a CRT 415.

A frequency/phase modulator 412 generates a driving signal which oscillates in the form of a sinusoidal wave. The frequency/phase modulator 412 can modulate the frequency of this driving signal. In addition, the frequency/phase modulator 412 can also modulate the phase of the driving signal, as needed. For this purpose, the frequency/phase modulator 412 comprises a sinusoidal wave oscillator for performing, e.g., frequency modulation, and a phase modulator arranged to be capable of being bypassed between the sinusoidal wave oscillator and an output terminal. A driver 411 serving as a voltage amplifier amplifies the driving signal output from the frequency/phase modulator 412 and is arranged to perform amplitude modulation under the control of a system controller 413. The amplified driving signal is supplied to each piezoelectric element of the ultrasonic source 402 through an impedance matching circuit 410. Each piezoelectric element generates an ultrasonic treatment wave at a frequency equal to that of the driving signal.

The system controller 413 serving as the control center of the entire apparatus is connected to a console 414. The console 414 has a switch for designating the start/stop of irradiation (treatment) of the ultrasonic treatment wave, switches for setting various treatment conditions, and other switches.

An operation of this embodiment will be described below. First, frequency modulation will be described. It is preferable that the piezoelectric elements be driven at a resonance frequency f0 unique to the thickness of the piezoelectric elements to generate ultrasonic treatment waves at the resonance frequency f0 from the viewpoint of conversion efficiency of electrical signal/mechanical vibrations. As well known, when an ultrasonic treatment wave is irradiated on a target object for a relatively long period of time while the frequency of the ultrasonic treatment wave is kept at the resonance frequency f0, a cavitation (bubble) gradually grows to a size which depends on its wavelength.

Figure 2A:
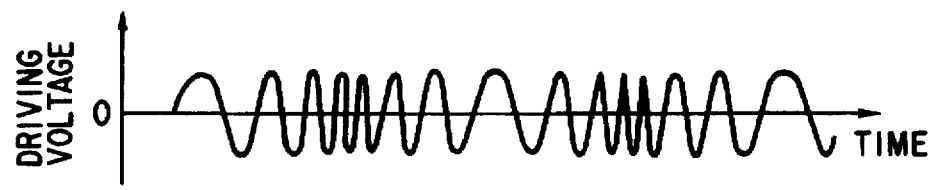
FIG. 2A is a chart showing one waveform of a frequency-modulated driving signal along the time axis.
Figure 2B:
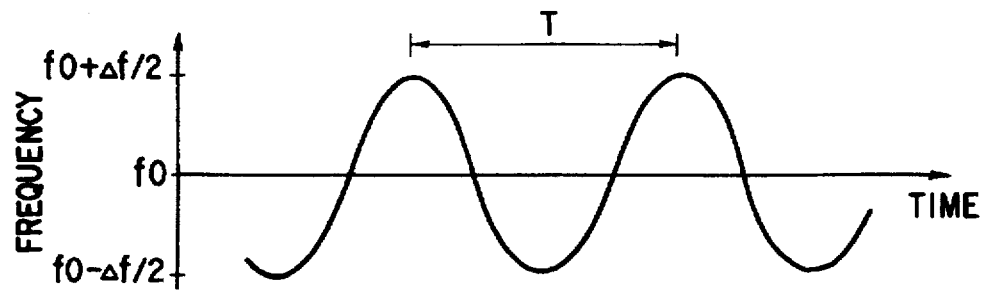
FIG. 2B is a chart showing a change in frequency of the driving signal in FIG. 2A along the time axis.

The system controller 413 controls the frequency/phase modulator 412 to change a frequency fm of the driving signal in the range of f0−Δf/2≦fm<f0+Δf/2 centered on the resonance frequency f0 along the time axis. The frequency of the driving signal is equal to that of the ultrasonic treatment wave generated by the ultrasonic source 402. In the following description, the "driving signal" equivalently represents the "ultrasonic treatment wave". FIGS. 2A, 3A, 4A, and 5A show the waveforms of various driving signals along the time axis, respectively. FIGS. 2B, 3B, 4B, and 5B show changes in frequencies of the corresponding driving signals along the time axis, respectively. An operator may select one of a plurality of types of driving signals, or one type of driving signal may be permanently selected. The driving signal in FIG. 2A is generated such that its frequency changes sinusoidally. The driving signal in FIG. 3A is generated such that its frequency changes stepwise. The driving signal in FIG. 4A is generated such that its frequency continuously changes with a predetermined gradient from a low frequency (f0−Δf/2) to a high frequency (f0+Δf/2). The driving signal in FIG. 5A is generated such that its frequency is alternately switched between a time interval in which the frequency is fixed to the resonance frequency f0 and a time interval in which the frequency changes sinusoidally.

Such a change in frequency along the time axis, i.e., a change in wavelength along the time axis suppresses growth of cavitation, divides grown cavitation, and reduces the sizes of growing cavitation. Therefore, all adverse influences caused by cavitation formed by cavitation can be eliminated.

Amplitude modulation of a driving signal will be described below. As shown in FIG. 6, the impedance on the piezoelectric element side when viewed from the driver 411 exhibits a minimum value at the resonance frequency f0 but has larger values at other frequencies. The conversion frequency of electrical signal/mechanical vibrations of the piezoelectric element exhibits a maximum value at the resonance frequency f0 and has smaller values at other frequencies. The degree of attenuation of an ultrasonic treatment wave in a living body depends on its frequency. The output energy of the ultrasonic treatment wave generated by the ultrasonic source 402 exhibits a maximum value at the resonance frequency and decreases at frequencies other than the resonance frequency f0. In this embodiment, the amplitude of the driving signal is modulated with its frequency, so that the output energy of the ultrasonic treatment wave is kept constant regardless of changes in frequency.

The system controller 413 controls the gain of the driver 411 in accordance with changes in frequency of the driving signal so as to maintain the output level of the ultrasonic treatment wave almost constant regardless of changes in frequency, thereby maintaining the input power to the ultrasonic source 402 constant. FIG. 7A shows the waveform of an amplitude-modulated driving signal, and FIG. 7B shows changes with time of the output energy of the ultrasonic treatment wave generated by the ultrasonic source 402 upon application of the amplitude-modulated driving signal. The amplitude of the amplitude-modulated driving signal exhibits a minimum value at the resonance frequency f0 and a maximum value at f0±Δf/2.

The impedance may be measured by an impedance measurement circuit and feedback control may be performed using this measurement value. Alternatively, the actual input power may be measured by a wattmeter, and feedback control may be performed using this measurement value.

In addition, as another method of correcting this output level, the variable inductance and capacitance values of the impedance matching circuit 410, which correspond to the frequency of the driving signal, may be stored in the internal memory of the system controller, and electrical matching may be controlled by the system controller 413 in accordance with the frequency.

The following method may be used in place of amplitude modulation or may be used together therewith as a method of reducing the output level variations of the ultrasonic treatment waves. According to this method, assuming that the wavelength of an ultrasonic wave at a frequency largely different from the resonance frequency f0 is defined as λ, an acoustic matching layer having a thickness λ/4 (λ=wavelength) is arranged on a piezoelectric element surface, and the output band is broadened to improve the output efficiency of the ultrasonic wave having the frequency greatly different from the resonance frequency.

Phase modulation will now be described. The phase modulation may be used together with the above frequency modulation. Alternatively, the driving signal fixed at the resonance frequency f0 is phase-modulated without performing the above frequency modulation. As shown in FIG. 8, the system controller 413 controls the frequency/phase modulator 412 to intermittently shift the phase of the driving signal 180° at a period T. Upon intermittent irradiation of ultrasonic treatment waves, cavitation gradually grow. When the phase of the ultrasonic treatment waves is inverted, the cavitation receive a pressure opposite to that upon growth. Therefore, cavitation thus grown is destroyed.

(Second Embodiment)

Figure 9:
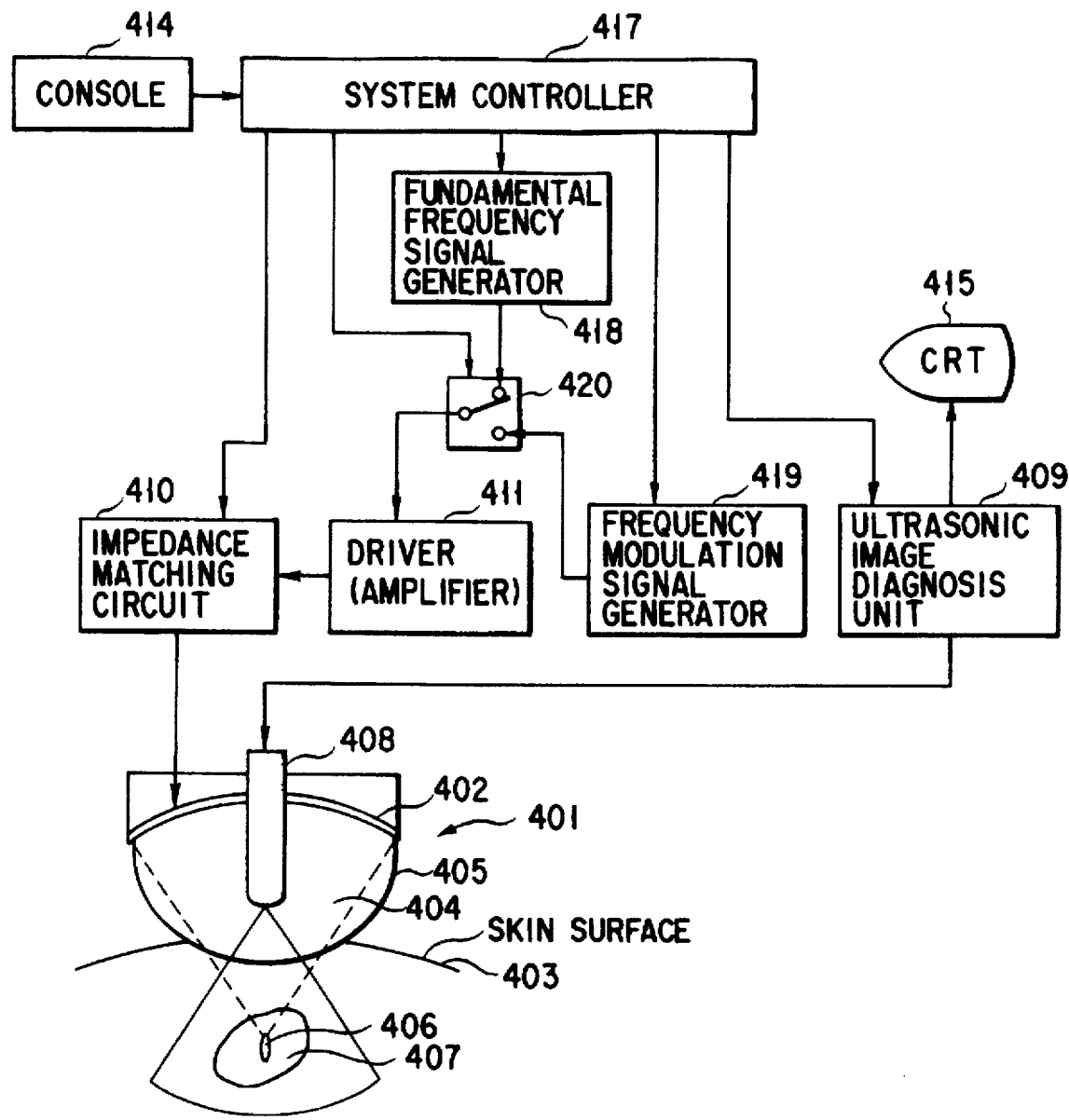
FIG. 9 is a block diagram showing an arrangement according to the second embodiment of the present invention.

FIG. 9 is a block diagram showing an ultrasonic treatment apparatus according to the second embodiment. The same reference numerals as in FIG. 1 denote the same parts in the second embodiment, and a detailed description thereof will be omitted. A fundamental frequency signal generator 418 is a circuit for causing a piezoelectric element to generate a driving signal at its unique resonance frequency f0. A frequency modulation signal generator 419 is a circuit for generating a driving signal whose frequency instantaneously changes along the time axis. A switch 420 alternately connects the fundamental frequency signal generator 418 and the frequency modulation signal generator 419 to a driver 411 under the control of a system controller 417. A driving signal generated by one of the fundamental frequency signal generator 418 and the frequency modulation signal generator 419 is amplified by the driver 411 through the switch 420. The amplified driving signal is supplied to each piezoelectric element of an ultrasonic source 402 through an impedance circuit 410.

Figure 10A:
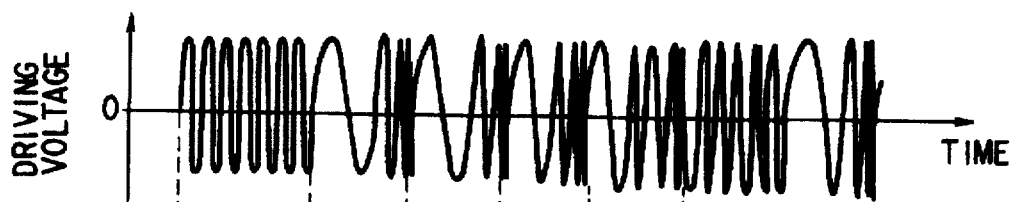
FIG. 10A is a chart showing the waveform of a frequency-modulated driving signal along the time axis.
Figure 10B:
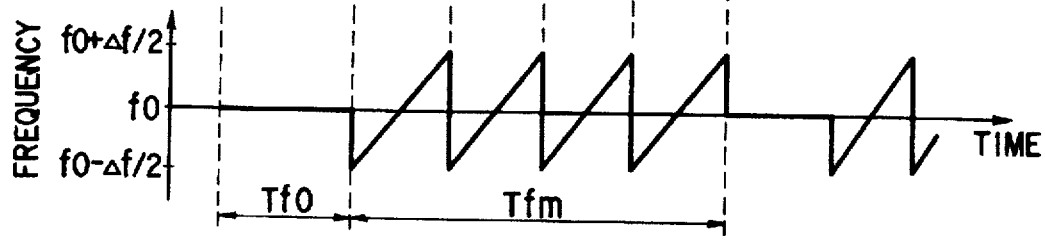
FIG. 10B is a chart showing a change in frequency of the driving signal in FIG. 10A along the time axis.

FIG. 10A shows the waveform of the driving signal output from the driver 411 along the time axis. FIG. 10B shows changes in frequency of the driving signal shown in FIG. 10A along the time axis. The fundamental frequency signal generator 418 and the frequency modulation signal generator 419 are alternately connected to the driver 411 by switching operations of the switch 420. The fundamental frequency signal generator 418 is intermittently connected to the driver 411 for a first interval Tf0, while the frequency modulation signal generator 419 is intermittently connected to the driver 411 for a second interval Tfm.

Figure 11A:
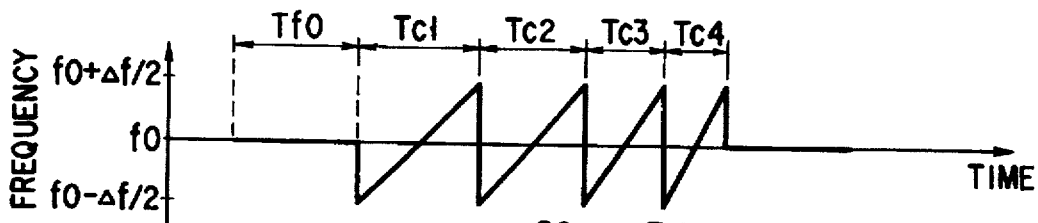
FIGS. 11A to 11C are timing charts showing other changes in frequencies of driving signals along the time axis.
Figure 11B:
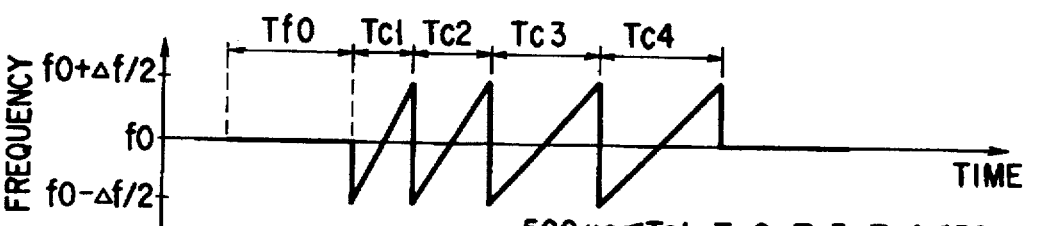
Figure 11C:
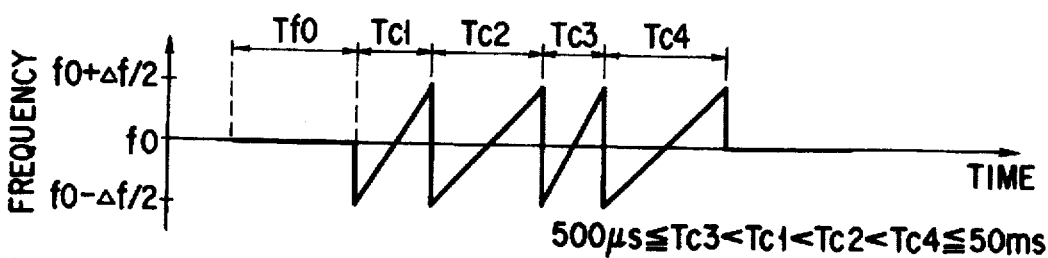

For the first interval Tf0, the ultrasonic source 402 is driven with a driving signal whose frequency is fixed to the resonance frequency f0, and an ultrasonic treatment wave is steadily generated at the resonance frequency f0. For the second interval Tfm, the ultrasonic source 402 is driven with a driving signal whose frequency instantaneously changes along the time axis, and an ultrasonic treatment wave whose frequency instantaneously changes along the time axis is generated. Any one of the changes in FIGS. 2B, 3B, and 4B may be used as a change in frequency along the time axis. In this case, the frequency fm linearly changes from a low frequency f0−Δf/2 to a high frequency f0+Δf/2, this change is repeated in a predetermined cycle time Tc; the driving signal changes in the form of a saw-tooth wave. In this case, the frequency fm may change with an opposite gradient, i.e., from the high frequency f0+Δf/2 to the low frequency f0−Δf/2. In addition, the cycle time Tc is not limited to be constant if it falls within a specific range (to be described later). As shown in FIGS. 11A, 11B, and 11C, the cycle time may be gradually shortened or prolonged, or may be irregularly changed.

FIG. 12 shows the relationship between the cycle time Tc and the cavitation amount. The cavitation amount is defined such that a cavitation amount obtained upon repeating continuous driving at the resonance frequency f0 and driving at a frequency changing along the time axis is represented by a relative value when a cavitation amount upon continuous driving at the resonance frequency f0 is given as 1. The efficiency of cavitation destruction depends on the rate of change in frequency, i.e., the length of the cycle time Tc when the frequency modulation width is assumed constant. The cycle time Tc is set within the range of 500 μs to 50 ms.

FIG. 13 shows the relationship between the second interval Tfm and the cavitation amount. The time required for destroying cavitation is longer than the time required for forming them. In this embodiment, the second interval Tfm is set three times or more the first interval Tf0 so as to sufficiently destroy the cavitation. When the second interval Tfm is excessively long, the first interval Tf0 for which the frequency is fixed to the resonance frequency f0 is shortened. For this reason, the time efficiency of the acoustic output is degraded, and the treatment time is undesirably prolonged. In this embodiment, in consideration of this point, the upper limit of the second interval Tfm is set 10 times the first interval Tf0.

FIG. 14 shows the relationship between the cavitation amount and the ratio (Δf/f0) of the frequency change width Δf to the resonance frequency f0. In this embodiment, the frequency change width Δf is set to 20% or more the resonance frequency f0. Although the upper limit of the frequency change width Δf is determined depending on the critical value for maintaining the conversion efficiency of electrical signal/mechanical vibrations of the piezoelectric element to a predetermined level, the upper limit is preferably set to 100% or less the frequency f0 in consideration of degradation of the conversion efficiency of the piezoelectric element.

The range of changes in the frequency fm is preferably set to satisfy the range f0−Δf/2≦fm≦f0+Δf/2 centered on the resonance frequency f0 in consideration of degradation in the piezoelectric element conversion efficiency when the frequency fm is separated from the resonance frequency f0. However, the range of changes in the frequency fm is not limited to this range. For example, as shown in FIG. 21A, Δf1 may be not equal to Δf2. As shown in FIG. 21B, "f0+Δf1>f0+Δf2>f0" may be made up.

According to this embodiment, an ultrasonic treatment wave having a maximum efficiency can be generated in respects of cavitation destruction and the treatment period.

(Third Embodiment)

FIG. 15 is a block diagram showing an ultrasonic treatment apparatus according to the third embodiment. The same reference numerals as in FIG. 1 denote the same parts in the third embodiment, and a detailed description thereof will be omitted. An ultrasonic treatment wave driver 431 generates a driving signal fixed at a resonance frequency f0 unique to the thickness of a piezoelectric element of an ultrasonic source (first ultrasonic source) 402 for treatment. This treatment driving signal is supplied to the ultrasonic source 402 through an impedance matching circuit 410 to generate an ultrasonic treatment wave. A cavitation destruction driver 432 generates a driving signal fixed at a frequency f' higher than the resonance frequency f0. The cavitation destruction driving signal is supplied to an ultrasonic source (second ultrasonic source) 434 for cavitation destruction separate from the ultrasonic source 402 through a second impedance matching circuit 433 to generate an ultrasonic cavitation destruction wave.

The ultrasonic source 434 for cavitation destruction comprises a plurality of piezoelectric elements arranged in a spherical pattern. To destroy the cavitation formed by the ultrasonic treatment waves, the piezoelectric elements are positioned and directed to irradiate the ultrasonic cavitation destruction wave to an area where cavitation are generated by the ultrasonic treatment wave, i.e., to the transmission path of the ultrasonic treatment wave.

The ultrasonic source 402 for treatment and the ultrasonic source 434 for cavitation destruction may be separately arranged, as described above. Alternatively, as shown in FIG. 17A, high-frequency piezoelectric elements constituting the ultrasonic source 434 for cavitation destruction may be located as central elements, and low-frequency piezoelectric elements constituting the ultrasonic source 434 for treatment may be located outside the central elements in a spherical pattern as a whole. As shown in FIG. 17B, piezoelectric elements having the resonance frequency f0 may be adhered in a two-layered structure. In this case, only one layer is driven to generate an ultrasonic treatment wave at the resonance frequency f0, while the two layers are simultaneously driven to generate an ultrasonic cavitation destruction wave at the high frequency f'.

FIGS. 16A to 16C show the waveforms of the driving signals of this embodiment. In FIG. 16A, the ultrasonic treatment wave having the relatively low frequency f0 and the ultrasonic cavitation destruction wave having the relatively high frequency f' are alternately irradiated. In FIG. 16B, the ultrasonic cavitation destruction wave is intermittently superposed on the ultrasonic treatment wave. In FIG. 16C, the ultrasonic waves having two frequencies (f0 and f') with a small difference are continuously superposed on each other to generate a "beat" signal, and the cavitation is destroyed using this beat signal.

As described above, according to the third embodiment, it is possible to forcibly destroy the cavitation generated upon irradiating the ultrasonic treatment wave. A side effect to an unwanted portion and a spread of the thermal degeneration area can be suppressed. At the same time, thermal degeneration can be accurately induced in a desired portion. A reliable, safe ultrasonic thermotherapy can be realized. Since cavitation caused by the cavitation can be suppressed, the ultrasonic energy can be continuously input to shorten the treatment period and increase the throughput.

(Fourth Embodiment)

In this embodiment, the cavitation amount is monitored. When the cavitation amount reaches a predetermined amount, an ultrasonic cavitation destruction wave is irregularly generated. FIG. 18 is a block diagram showing an ultrasonic treatment apparatus according to the fourth embodiment. The same reference numerals as in FIG. 1 denote the same parts in the fourth embodiment, and a detailed description thereof will be omitted. Ultrasonic image data generated by an ultrasonic image diagnosis unit 409 is supplied to a CRT 415 and a difference circuit 416.

An ultrasonic image generated by the ultrasonic image diagnosis unit 415 when no cavitation or a very small number of cavitation are generated, as shown in FIG. 19A, is stored as a mask image in the internal memory of the difference circuit 416. This mask image does not have cavitation images or has a very small number of cavitation images.

FIG. 19B shows an ultrasonic image (real-time image) generated by the ultrasonic image diagnosis unit 415 immediately after irradiation of the ultrasonic treatment wave. The ultrasonic treatment wave is intermittently irradiated as a burst wave, a slice near the focal point is scanned with the ultrasonic imaging beam at the irradiation interval of the ultrasonic treatment wave, and ultrasonic images of this slice are repeatedly generated. The number of cavitation images gradually increases with an increase in irradiation time of the ultrasonic treatment wave.

The differences between the real-time images and the mask images are calculated to sequentially generate difference images shown in FIG. 19C. The difference image data is supplied to a system controller 413. The system controller 413 obtains, as a difference level, the sum of the pixel values of a plurality of pixels within a specific area of the difference image. FIG. 20A shows transitions in difference level along the time axis. The difference level depends on the generated cavitation amount. Note that the specific area is set as a propagation area of the ultrasonic treatment wave up to the focal point at which cavitation are assumed to be generated.

The system controller 413 compares the resultant difference level with a threshold level. When the difference level is lower than the threshold level, the system controller 413 generates an ultrasonic treatment wave at the resonance frequency f0, as shown in FIG. 20B, and controls a frequency/phase modulator 412 so as to continue the thermotherapy.

During an interval in which the difference level exceeds the threshold level, in order to positively destroy cavitation, the system controller 413 controls the frequency/phase modulator 412 so as to change the frequency, as shown in FIG. 20B.

When the difference level exceeds the threshold level, the system controller 413 controls the frequency/phase modulator 412 to invert the phase of the ultrasonic treatment wave, as shown in FIG. 20C, while maintaining the frequency at the resonance frequency f0 in addition to this change in frequency.

In this manner, cavitation can be appropriately destroyed, and a decrease in treatment rate can be prevented.

According to the present invention, since the cavitation formed upon irradiation of the ultrasonic treatment wave can be effectively suppressed, a side effect to an unwanted portion and a spread of the thermal degeneration area can be more effectively suppressed than the conventional method. At the same time, thermal degeneration can be accurately induced in a desired portion, thereby realizing a more reliable, safer ultrasonic thermotherapy. In addition, the total treatment period can be reduced to increase the throughput.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic treatment apparatus for raising tissue temperature for thermotherapy treatments, comprising:
   an ultrasonic source for generating an ultrasonic treatment wave; and
   driving means for driving said ultrasonic source such that a frequency of the ultrasonic treatment wave generated by said ultrasonic source changes along a time axis such that cavitation is suppressed.

2. An apparatus according to claim 1, wherein said driving means includes driving signal generating means for generating a driving signal to said ultrasonic source and means for controlling said driving signal generating means.

3. An apparatus according to claim 1, wherein said driving means modulates an amplitude of a driving signal in accordance with the frequency of the ultrasonic treatment wave such that an output level of the ultrasonic treatment wave generated by said ultrasonic source is kept at a substantially constant level.

4. An apparatus according to claim 1, wherein the frequency of the ultrasonic treatment wave changes from a low frequency to a high frequency.

5. An apparatus according to claim 1, wherein the frequency of the ultrasonic treatment wave repeatedly changes at a period within a range of 500 µs to 50 ms.

6. An apparatus according to claim 1, wherein said driving means drives said ultrasonic source such that a first interval in which the frequency of the ultrasonic treatment wave is fixed to a specific frequency and a second interval in which the frequency of the ultrasonic treatment wave changes along the time axis; and said driving means alternates between said first and second interval.

7. An apparatus according to claim 6, wherein the specific frequency is set to a resonance frequency of at least one ultrasonic element of said ultrasonic source.

8. An apparatus according to claim 6, wherein the frequency of the ultrasonic treatment wave repeatedly changes at a period within a range of 500 µs to 50 ms in the second interval.

9. An apparatus according to claim 6, wherein the second interval is set not more than three times the first interval.

10. An apparatus according to claim 6, wherein the second interval is set not less than three times the first interval and not more than 10 times the first interval, and the frequency of the ultrasonic treatment wave repeatedly changes at a period within a range of 500 µs to 50 ms in the second interval.

11. An apparatus according to claim 1, wherein the frequency of the ultrasonic treatment wave changes within a range of at least 20% the resonance frequency unique to said ultrasonic source.

12. An apparatus according to claim 1, further comprising:

means for scanning a slice of a target object with an ultrasonic beam to repeatedly generate ultrasonic images on the basis of resultant reception signals;

difference means for obtaining a difference between two ultrasonic frame images generated at different times; and means for counting, on the basis of a difference result from said difference means, timings at which the frequency of the ultrasonic treatment wave is changed.

13. The apparatus according to claim 1, wherein said driving means changes said frequency to break at least part of bubbles which appear with generation of said ultrasonic treatment wave.

14. The apparatus according to claim 1, further comprising an imaging probe for transmitting an ultrasonic wave for imaging, and for receiving an echo from a subject.

15. An ultrasonic treatment apparatus comprising:

an ultrasonic source for generating an ultrasonic treatment wave; and driving means for driving said ultrasonic source such that a phase of the ultrasonic treatment wave generated by said ultrasonic source is modulated.

16. An apparatus according to claim 15, wherein the phase of the ultrasonic treatment wave is intermittently inverted.

17. An apparatus according to claim 15, further comprising:

means for scanning a slice of a target object with an ultrasonic beam to repeatedly generate ultrasonic images on the basis of resultant reception signals;

difference means for obtaining a difference between two ultrasonic frame images generated at different times; and means for counting, on the basis of a difference result from said difference means, timings at which the phase of the ultrasonic treatment wave is modulated.

18. An ultrasonic treatment apparatus comprising:

a first ultrasonic source for generating an ultrasonic treatment wave;

a second ultrasonic source for generating an ultrasonic cavitation destruction wave having a frequency higher than that of the ultrasonic treatment wave; and driving means for driving said first and second ultrasonic sources.

19. An apparatus according to claim 18, wherein said first and second ultrasonic sources are formed in a spherical pattern as a whole, said second ultrasonic source is located near the center, and said first ultrasonic source is located around said second ultrasonic source.

20. An apparatus according to claim 18, wherein the ultrasonic treatment wave is generated by a first piezoelectric layer, and the ultrasonic cavitation destruction wave is generated by simultaneously driving said first piezoelectric layer and a second piezoelectric layer stacked on said first piezoelectric layer.

21. An apparatus according to claim 18, wherein said driving means alternatively drives said first and second ultrasonic generators.

22. An apparatus according to claim 18, wherein said driving means simultaneously drives said first and second ultrasonic sources.

* * * * *